(12) United States Patent
Molz et al.

(10) Patent No.: US 8,142,476 B2
(45) Date of Patent: Mar. 27, 2012

(54) ORTHOPEDIC DISTRACTION IMPLANTS AND TECHNIQUES

(75) Inventors: Fred J. Molz, Collierville, TN (US); Jeff R. Justis, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 452 days.

(21) Appl. No.: 11/983,911

(22) Filed: Nov. 13, 2007

(65) Prior Publication Data

US 2008/0071373 A1    Mar. 20, 2008

Related U.S. Application Data

(62) Division of application No. 10/768,797, filed on Jan. 30, 2004, now Pat. No. 7,297,146.

(51) Int. Cl.
*A61B 17/70* (2006.01)

(52) U.S. Cl. .................................................. 606/246

(58) Field of Classification Search .............. 606/72, 606/90, 246–279; 623/17.11
See application file for complete search history.

(56) References Cited

U.S. PATENT DOCUMENTS

| | | | |
|---|---|---|---|
| 2,580,821 A | 1/1952 | Nicola | |
| 3,565,066 A | 2/1971 | Roaf et al. | |
| 3,865,105 A | 2/1975 | Lode | |
| 3,977,397 A | 8/1976 | Kalnberz et al. | |
| 4,078,559 A | 3/1978 | Nissinen | |
| 4,263,904 A | 4/1981 | Judet | |
| 4,369,770 A | 1/1983 | Bacal et al. | |
| 4,386,603 A | 6/1983 | Mayfield | |
| 5,147,360 A | 9/1992 | Dubousset | |
| 5,246,443 A | 9/1993 | Mai | |
| 5,282,863 A | 2/1994 | Burton | |
| 5,415,661 A * | 5/1995 | Holmes | 606/255 |
| 5,540,688 A | 7/1996 | Navas | |
| 5,609,634 A | 3/1997 | Voydeville | |
| 5,672,175 A * | 9/1997 | Martin | 606/86 A |
| 5,681,313 A | 10/1997 | Diez | |
| 5,683,390 A | 11/1997 | Metz-Stavenhagen et al. | |
| 5,702,395 A | 12/1997 | Hopf | |
| 5,779,707 A | 7/1998 | Bertholet et al. | |
| 5,785,713 A | 7/1998 | Jobe | |
| 5,961,516 A | 10/1999 | Graf | |
| 5,993,476 A | 11/1999 | Groiso | |
| 6,015,409 A | 1/2000 | Jackson | |
| 6,019,760 A | 2/2000 | Metz-Stavenhagen et al. | |

(Continued)

FOREIGN PATENT DOCUMENTS

DE   28 21 678 A1   11/1979

(Continued)

OTHER PUBLICATIONS

DYNESYS The Spinal Implant for Dynamic Re-stabilization of Spinal Segments in Case of Intervertebral Disc Damage; Sulzer Medica Annual Report; 1999.

(Continued)

*Primary Examiner* — Eduardo C Robert
*Assistant Examiner* — Summer Kostelnik

(57) ABSTRACT

An implant for stabilizing a bony segment includes a flexible body sized and shaped to extend intravertebrally between at least first and second bony portions. In use the body is attachable intravertebrally to each of the first and second bony portions to distract each of the first and second bony portions while allowing motion between each of the first and second bony portions.

20 Claims, 9 Drawing Sheets

U.S. PATENT DOCUMENTS

| | | |
|---|---|---|
| 6,019,793 A | 2/2000 | Perren et al. |
| 6,132,431 A | 10/2000 | Nilsson et al. |
| 6,224,599 B1 | 5/2001 | Baynham et al. |
| 6,241,746 B1 | 6/2001 | Bosma et al. |
| 6,290,700 B1 | 9/2001 | Schmotzer |
| 6,293,949 B1 | 9/2001 | Justis et al. |
| 6,325,805 B1 * | 12/2001 | Ogilvie et al. ............ 606/75 |
| 6,402,750 B1 | 6/2002 | Atkinson et al. |
| 6,440,169 B1 | 8/2002 | Elberg et al. |
| 6,530,929 B1 | 3/2003 | Justis et al. |
| 6,565,605 B2 * | 5/2003 | Goble et al. ............ 623/17.11 |
| 6,616,669 B2 | 9/2003 | Ogilvie et al. |
| 6,623,484 B2 | 9/2003 | Betz et al. |
| 6,743,257 B2 | 6/2004 | Castro |
| 6,783,531 B2 * | 8/2004 | Allen ............ 606/75 |
| 6,966,910 B2 * | 11/2005 | Ritland ............ 606/257 |
| 6,966,911 B2 | 11/2005 | Groiso |
| 2002/0026242 A1 | 2/2002 | Boyle et al. |
| 2003/0083657 A1 | 5/2003 | Drewry et al. |
| 2004/0002708 A1 | 1/2004 | Ritland |
| 2004/0172040 A1 | 9/2004 | Heggeness |
| 2005/0021035 A1 | 1/2005 | Groiso |
| 2005/0049600 A1 | 3/2005 | Groiso |
| 2005/0273108 A1 | 12/2005 | Groiso |

FOREIGN PATENT DOCUMENTS

| | | |
|---|---|---|
| EP | 0 667 127 A1 | 8/1995 |
| EP | 0 669 109 B1 | 8/1995 |
| WO | WO 96/01598 | 1/1996 |
| WO | WO 02/102259 | 12/2002 |

OTHER PUBLICATIONS

Dynamic Re-stabilization of Spinal Segments; Sulzer Technical Review; 1999.

* cited by examiner

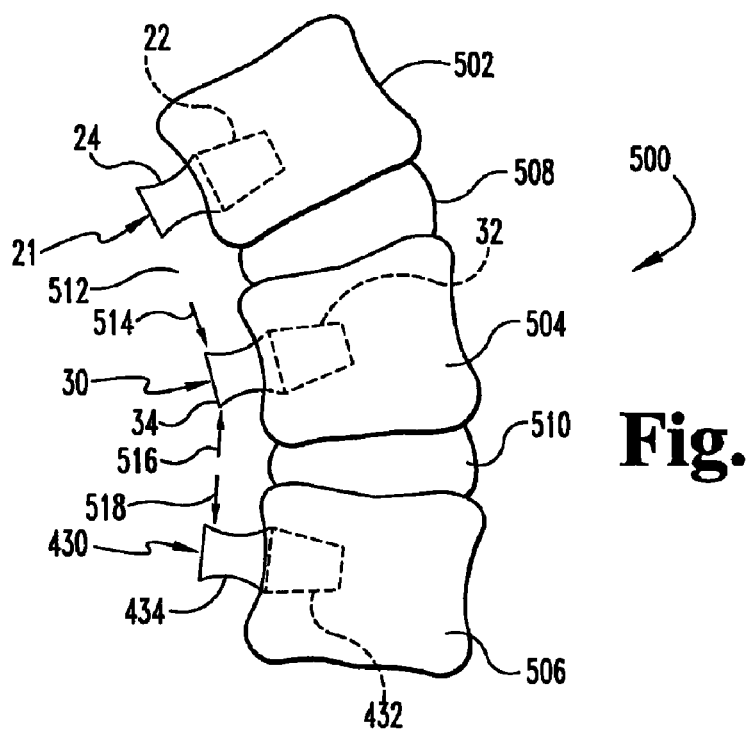
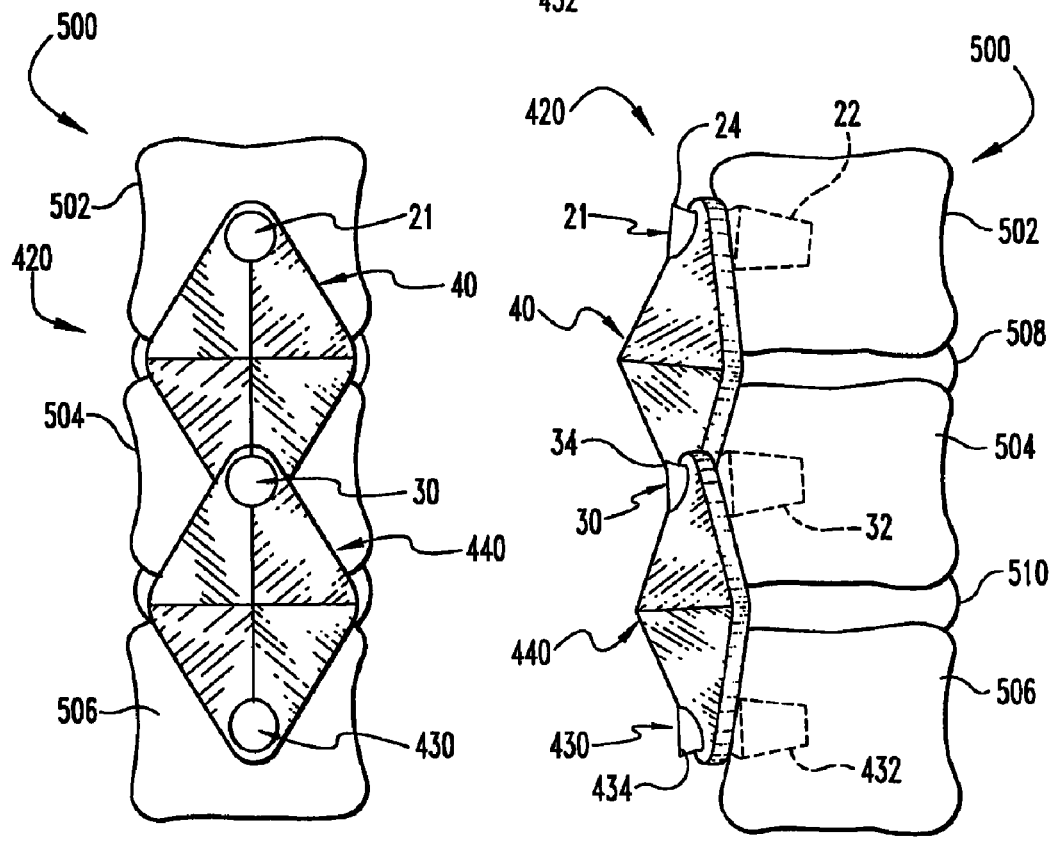
Fig. 7
Fig. 8         Fig. 9

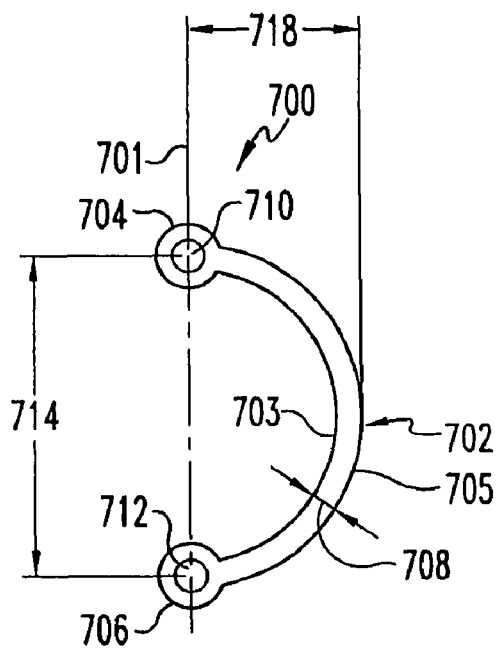
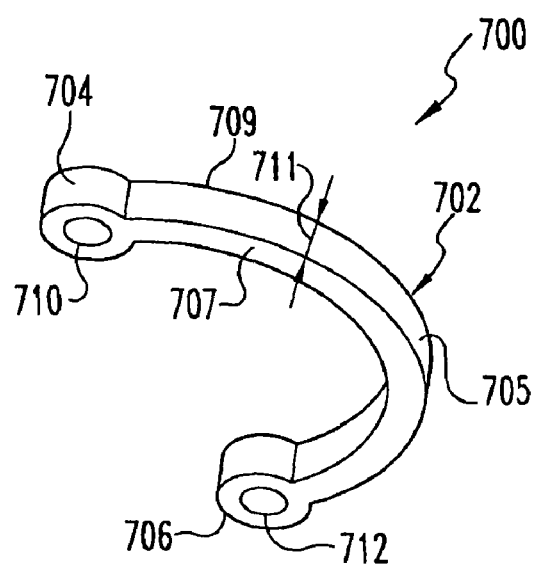
Fig. 13     Fig. 14
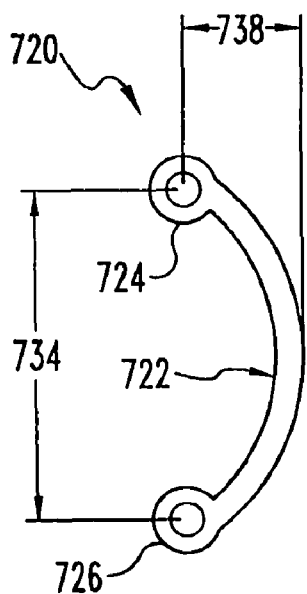
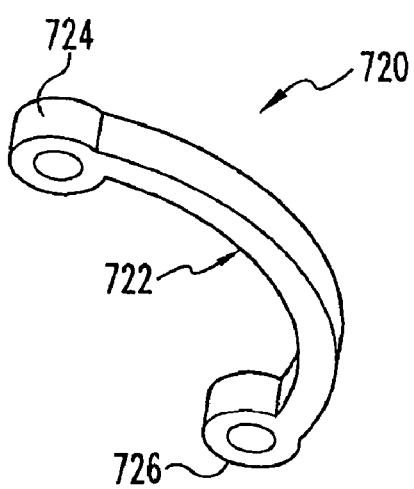
Fig. 15     Fig. 16

US 8,142,476 B2

ORTHOPEDIC DISTRACTION IMPLANTS AND TECHNIQUES

CROSS-REFERENCE TO RELATED APPLICATION

This application is a divisional of U.S. patent application Ser. No. 10/768,797, filed Jan. 30, 2004, now U.S. Pat. No. 7,297,146, which is incorporated herein by reference in its entirety.

BACKGROUND

Adjacent bony portions can require treatment to obtain the desired surgical result. For example, the adjacent bony portions may require the application and/or maintenance of distraction forces therebetween in order to provide proper positioning and alignment of the adjacent bony portions for the desired surgical correction and healing to occur. There remains a need for implants and techniques that facilitate surgical correction of adjacent bony portions with distraction forces.

SUMMARY

To facilitate surgical correction of adjacent bony portions, an implant includes a body attachable to adjacent bony portions adapted to apply and/or maintain a distraction force between the adjacent bony portions.

According to one aspect, an implant for treating a bony segment includes a body attachable intravertebrally to each of the first and second bony portions and adapted to apply and/or maintain a distraction force between each of the first and second bony portions while allowing motion between each of the first and second bony portions.

According to another aspect, an implant for distracting adjacent bony portions includes a body with a first condition and a second condition. The body extends intravertebrally between the adjacent bony portions for attachment thereto in the second condition. When attached, the body returns toward the first condition to apply a distraction force to the adjacent bony portions.

In a further aspect, a system for distracting adjacent bony portions includes a first anchor and a second anchor engageable to respective ones of the adjacent bony portions. An implant body extends intravertebrally of the adjacent bony portions and is attached to the first and second anchors. The body applies a distraction force between the first and second anchors when attached thereto.

According to another aspect, a method for correcting a curved portion of a spinal column segment includes attaching an implant on a concavely curved side of the spinal column segment; and applying a distraction load to the concave side with the implant.

According to another aspect, a method for correcting a curved portion of a spinal column segment includes providing an implant having a first condition wherein the ends of the implant are spaced a first distance, a second condition wherein the ends of the implant are spaced a second distance less than the first distance; attaching the implant to a concave side of the spine in the second condition; and biasing the implant from the second condition to the first condition to apply a distraction load.

In another aspect, a method for distracting adjacent vertebrae of a spinal column segment includes positioning an implant extradiscally along the adjacent vertebrae; attaching the implant to the adjacent vertebrae; and applying a distraction load to the adjacent vertebrae with the implant.

These and other aspects of the disclosure are also discussed below.

BRIEF DESCRIPTION OF THE DRAWINGS

FIG. 7 is an elevation view looking in the anterior-posterior direction at a concavely curved portion of a spinal column segment with anchors engaged thereto.

FIG. 8 is an elevation view looking in the medial-lateral direction toward the concavely curved portion of the spinal column segment of FIG. 7 with distraction implants of FIG. 1 secured thereto.

FIG. 9 is an anterior-posterior elevation view of the spinal column segment and distraction implants of FIG. 8.

FIG. 13 is an elevation view of another embodiment distraction implant.

FIG. 14 is a perspective view of the distraction implant of FIG. 13.

FIG. 15 is an elevation view of another embodiment distraction implant.

FIG. 16 is a perspective view of the distraction implant of FIG. 15.

DESCRIPTION OF THE ILLUSTRATED EMBODIMENTS

Figure 1:
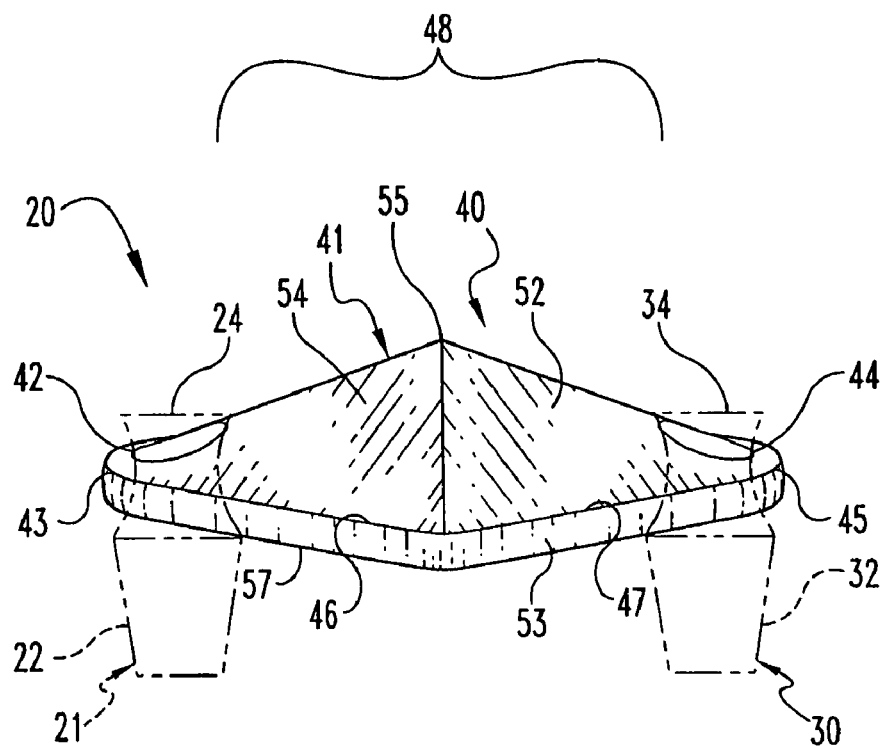
FIG. 1 is an elevation view of one embodiment of a distraction implant.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein are contemplated as would normally occur to one skilled in the art to which the invention relates.

In FIG. 1 there is shown a treatment system 20 that includes a distraction implant 40. Distraction implant 40 includes a body 41 with a length extending along a longitudinal axis 49 (FIG. 2) sized to extend between adjacent bony portions for attachment of body 41 thereto. Distraction implant 40 can be attached intravertebrally to adjacent bony portions with a first anchor 21 and a second anchor 30 engageable to respective ones of the adjacent bony portions. In the illustrated embodiment, first anchor 21 includes a distal bone engagement portion 22 and a proximal attachment portion 24. Second anchor 30 also includes a distal bone engagement portion 32 and a proximal attachment portion 34. Body 41 of distraction implant 40 extends between and is attached to attachment portions 24, 34 of anchors 21, 30, respectively.

To facilitate attachment to anchors 21, 30, distraction implant 40 can be provided with a first hole 42 adjacent a first end 43 of body 41 and a second hole 44 adjacent a second end 45 of body 41. First and second holes 42, 44 can be sized to receive proximal attachment portions 24, 34 of anchors 21, 31 therein. Other embodiments contemplate that distraction implant 40 could be configured at each end thereof for attachment to two or more anchors engaged to respective ones of the adjacent bony portions. Holes 21, 30 can include a broad and deep configuration to maximize the surface area contact between distraction implant 40 and each of the anchors 21, 30. It is also contemplated that anchors can be positioned by penetrating body 41 with the anchors.

It is contemplated that body 41 can be made from a suitable material that allows body 41 to maintain the desired spatial relationship between the adjacent bony portions. Body 41 can continuously maintain and/or exert a distraction force between anchors 21, 30 without rigidly fixing the adjacent bony portions to one another. For example, body 41 can include a first condition in which its ends are spaced from one another a first distance. Body 41 is formable to a second condition in which its ends are moved toward one another and spaced a second distance that is less than the first distance. Body 41 can be formed by compression, deformation, unexpanding or other transformation to the second condition. Body 41 is released, reformed, expanded, or otherwise transformed from the second condition to the first condition to provide a distraction force between the vertebrae to which it is attached.

In use, body 41 can be attached in its second conditions to anchors 21, 30. After attachment, body 41 returns toward its first condition to exert and/or maintain a distraction force between anchors 21, 30. It is also contemplated that a distraction force can be applied to anchors 21, 30 with a distraction instrument, and distraction implant 40 can be attached to the distracted anchors 21, 30 to at least partially maintain the distraction force applied thereto. It is further contemplated that a distraction force can be applied between anchors 21, 30 and distraction implant 40 can in its second condition be attached to the distracted anchors 21, 30, and return toward its first condition after attachment to anchors 21, 30 to maintain or increase the distraction force between anchors 21, 30.

Various materials are contemplated for body 41, including gels, elastomers, visco-elastic gels or plastics, foams, fabrics, meshes, shape memory alloys, other suitable biocompatible materials, and combinations thereof. Anchors 21, 30 can be of the type configured to provide bony incorporation into the bony portion in which the anchor is engaged. Examples of such anchors are provided in U.S. patent application Ser. No. 10/137,038, filed on May 2, 2002, which is incorporated herein by reference in its entirety. It is also contemplated that anchors 21, 30 could be provided in the form of bone screws, including cannulated bone screws and multi-axial bone screws, staples, suture anchors, spikes, bolts, interbody fusion devices positioned between adjacent bony portions, interbody implants positioned between adjacent bony portions, and other devices suitable for engaging bony structure.

Body 41 includes a length in the direction of longitudinal axis 49 and a width in the direction of medial axis 51. In the illustrated embodiment, the width of body 41 varies along longitudinal axis 49. As shown in FIG. 1, body 41 includes a base portion 53 extending between first end 43 and second end 45. A lower surface 57 of body 41 extends along base portion 53, and is positionable adjacent the bony portions to which distraction implant 40 is to be attached. Base portion 53 can be provided with a substantially constant thickness along the length and width of body portion 41. A variable stiffness portion of distraction implant 40 in the form of an enlarged mid-portion 48 extends opposite lower surface 57 from base portion 53.

Medial axis 51 separates body 41 into a first portion 46 and a second portion 47. First portion 46 of body 41 includes a first upper surface 48 on one side of longitudinal axis 49, and a second upper surface 54 on the opposite side of longitudinal axis 49. On the other side of medial axis 51, second portion 47 of body 41 includes a third upper surface 50 along one side of longitudinal axis 49, and a fourth upper surface 52 along the other side of longitudinal axis 49. The adjacent upper surfaces 48 and 54 can meet along or adjacent longitudinal axis 49, and the adjacent upper surfaces 50 and 52 can meet along or adjacent longitudinal axis 49. The adjacent upper surfaces 48 and 50 can meet along or adjacent medial axis 51, and the adjacent upper surfaces 52 and 54 can meet along or adjacent medial axis 51.

Each of the surfaces 48, 50, 52, 54 can meet at an apex 55 formed at or adjacent the intersection of longitudinal axis 49 and medial axis 51. It is contemplated apex 55 provides a region or point of maximum thickness for body 41 along mid-portion 48. Surfaces 48, 50, 52, 54 of body 41 can taper from apex 55 towards outer edges of body 41. In the illustrated embodiment, surfaces 48, 50, 52, 54 are planar and form a pyramidal shape. Also contemplated are fewer or additional upper surfaces forming other polygonal shapes, and that any one or all of the surfaces 48, 50, 52, 54 can be provided with curvature such that body 41 includes a bulbous or rounded shape.

Figure 2:
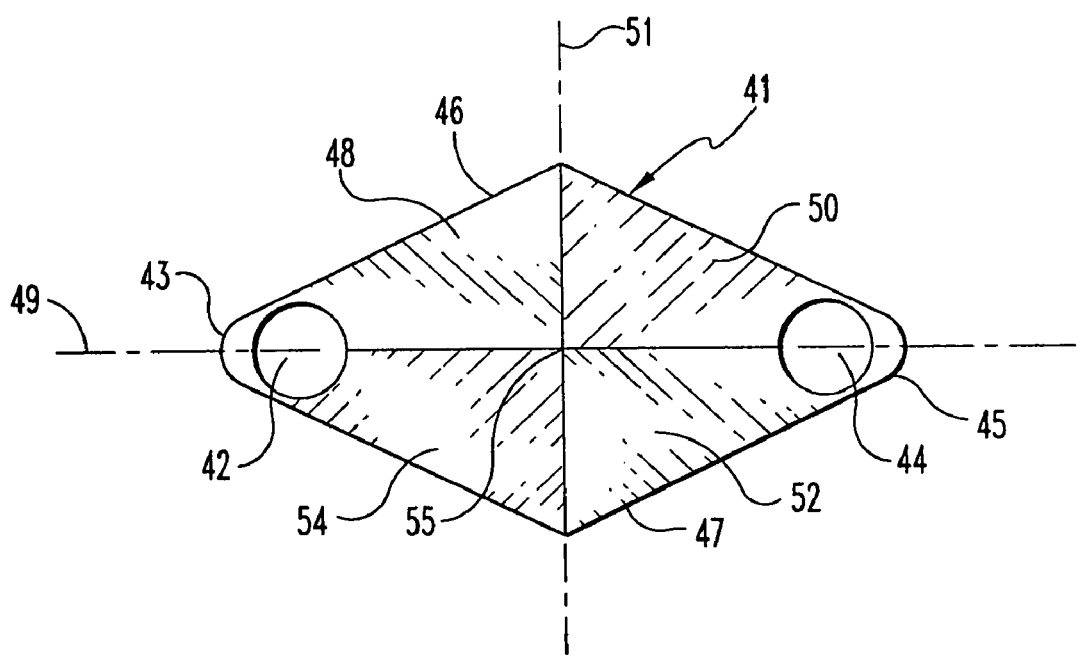
FIG. 2 is a plan view of the distraction implant of FIG. 1.

In the embodiment illustrated in FIGS. 1 and 2, the upper surfaces of body 41 provide body 41 with a greatest thickness at or adjacent the intersection of longitudinal axis 49 and medial axis 51. Accordingly, the resistance of body 41 to forces which tend to compressively deform body 41 increases from each of the ends 43, 45 of body 41 toward apex 55. Mid-portion 48 can be sized to prevent body 41 from buckling under the expected compressive loads. The amount of compressive deformation of body 41 can be limited under the expected compressive loads to maintain a minimum spacing between ends 43, 45, yet allow ends 43, 45 to move relative to one another so that the adjacent bony portions are not rigidly fixed to one another.

Figure 3:
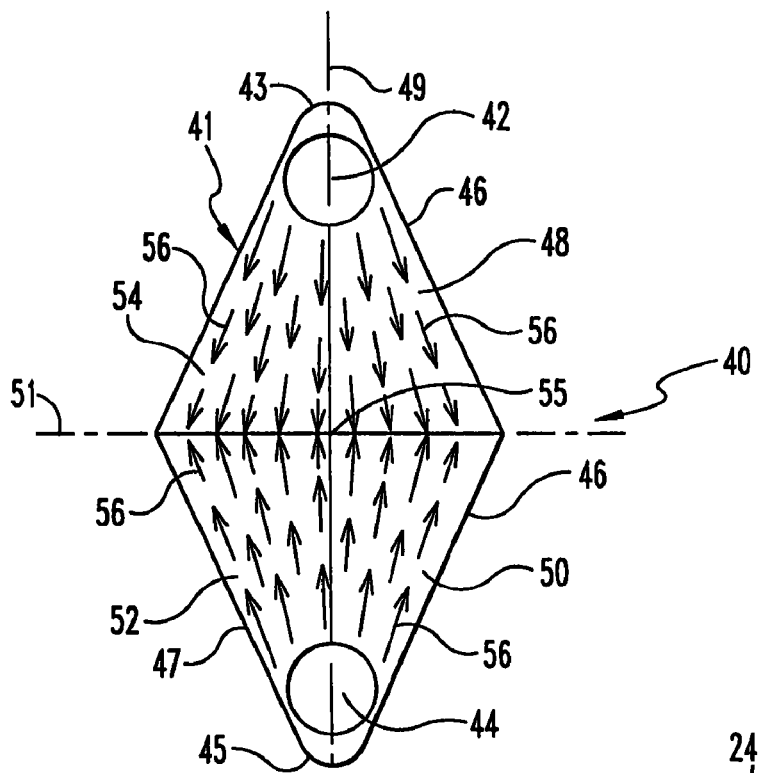
FIG. 3 is a plan view of the distraction implant of FIG. 1 showing a compression force distribution pattern.

FIG. 3 shows distraction implant 40 with a compressive force dissipation pattern superimposed thereon as represented by force arrows 56. Such compressive forces can be created by static and dynamic compressive loading on distraction implant 40 by the adjacent bony portions. The compressive force per unit of cross-sectional area will be highest immediately adjacent holes 42, 44 wherein the material cross-sectional area is the least. The width and height of body 41 each increase from ends 43, 45 toward apex 55, providing variable stiffness properties to body 41 along its length. The compressive force per unit of cross-sectional area reduces from ends 43, 45 toward apex 55, thus reducing the deformation of body 41 due to compressive forces. Body 41 can function as a shock absorbing device that can be compressed to provide a second condition for attachment and sufficiently elastic to return toward its uncompressed, first condition to apply or maintain distraction loading between anchors 21 and 30. The flexible body 41 also allows some movement of the adjacent bony portions relative to one another. The variable stiffness properties of body 41 limits this movement to maintain stabilization of the adjacent bony portions.

Specific embodiments of distraction implant 40 are configured for application in the spinal region to maintain and/or provide distraction between adjacent vertebral bodies while preserving, at least partially, segmental motion between the vertebral bodies. For such spinal applications, it is contemplated that body 41 can be provided with an overall length in the direction of longitudinal axis 49 in the range from 2 to 4 centimeters between adjacent sides of holes 42 and 44. Holes 42, 44 can be provided with a diameter ranging from 1 to 2 centimeters. Body 41 can be provided with a maximum width in the direction of medial axis 51 in the range from 2 to 4 centimeters. Body 41 can be provided with a maximum height from bottom surface 57 to apex 55 in the range from about 1 to 3 centimeters. It is to be understood that such dimensions can vary and other dimensions are contemplated based on, for example, patient anatomy, the region of the body of the patient in which distraction implant 40 is to be attached, the properties of the material comprising distraction implant 40, and expected loading on the distraction implant 40.

Figure 4:
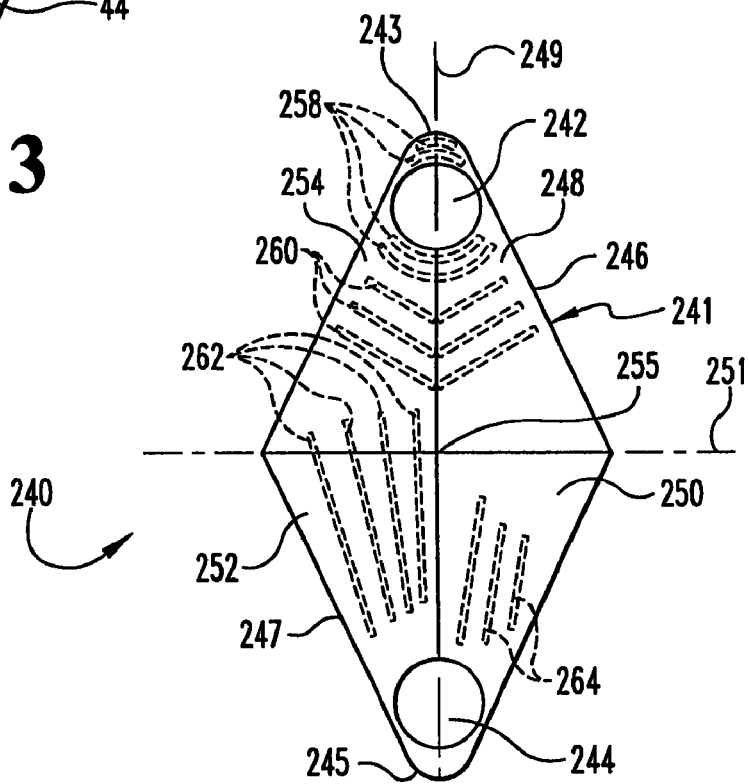
FIG. 4 is a plan view of another embodiment distraction implant.

Referring to FIG. 4, another embodiment distraction implant 240 includes a body 241 and first and second holes 242, 244 adjacent ends 243, 245, respectively. Body 241 can be provided as discussed above with respect to body 41 of distraction implant 40. Body 241 extends along longitudinal axis 249, and medial axis 251 divides body 241 into a first portion 246 and a second portion 247. Body 241 can be provided with upper surface portions 248, 250, 252, 254 that are positioned entirely or primarily in respective quadrants formed by the intersection of axes 249, 251. Surfaces 248, 250, 252, 254 provide an enlarged mid-portion extending from apex 255 adjacent or at the intersection of the longitudinal and medial axes 249, 251.

Distraction implant 240 can be provided with one or more reinforcing members in body 241 to assist in maintaining the structural integrity of body 241 and provide variable stiffness properties thereto. For example, reinforcing members 258 can be provided around one or more of the anchor holes through body 241, such as shown with respect to hole 242. Reinforcing members 258 can be provided medially of hole 242 to assist body 241 in resisting compressive forces. Reinforcing members 258 can be provided between hole 242 and end 243 to assist body 241 and reinforcing members 258 in resisting tensile forces. Reinforcing members 258 can have a curved shape to extend around the adjacent hole 242 to provide reinforcement in areas of body 241 subject to high stress concentrations applied by the anchor extending through the adjacent hole.

Medially oriented reinforcing members 260 can be provided, for example, in first portion 246 that extend across longitudinal axis 249 to assist body 241 in resisting compression and tensile forces. The ends of reinforcing members 260 can extend from longitudinal axis 249 and away from medial axis 251 toward the end of the implant, such as end 243, to provide longitudinal resistance to compressive and distraction loading. The medially extending component of reinforcing members 261 can resist torsional or twisting forces applied to body 241. Other embodiments contemplate medially oriented reinforcement members that extend from longitudinal axis 249 toward medial axis 251, that extend parallel to medial axis 251, and combinations thereof.

First longitudinally oriented reinforcing members 262 extend across medial axis 251 between first portion 246 and second portion 247 of body 241. Reinforcing members 262 extend primarily longitudinally in the direction of longitudinal axis 249. Second longitudinal reinforcing members 264 can be provided that are located in body 241 in one of the first and second portions 246, 247, such as shown in second portion 247. Body 241 can be provided with any one or combination of reinforcing members 258, 260, 262, 264 discussed above. Other embodiments contemplate reinforcing members randomly distributed through body 241 in linear and non-linear arrangements.

Various forms for reinforcing members 258, 260, 262, 264 are contemplated. The reinforcing members can be in the form of increased material density, or in the form of a material that differs from the material of body 241. Examples include bars, strips, fibers or filaments made from metallic, plastic or other suitable material. Reinforcing members 258, 260, 262, 264 can be embedded in body 241, or extend along one or more of the upper surface portions, or along the lower surface of body 241.

Figure 5:
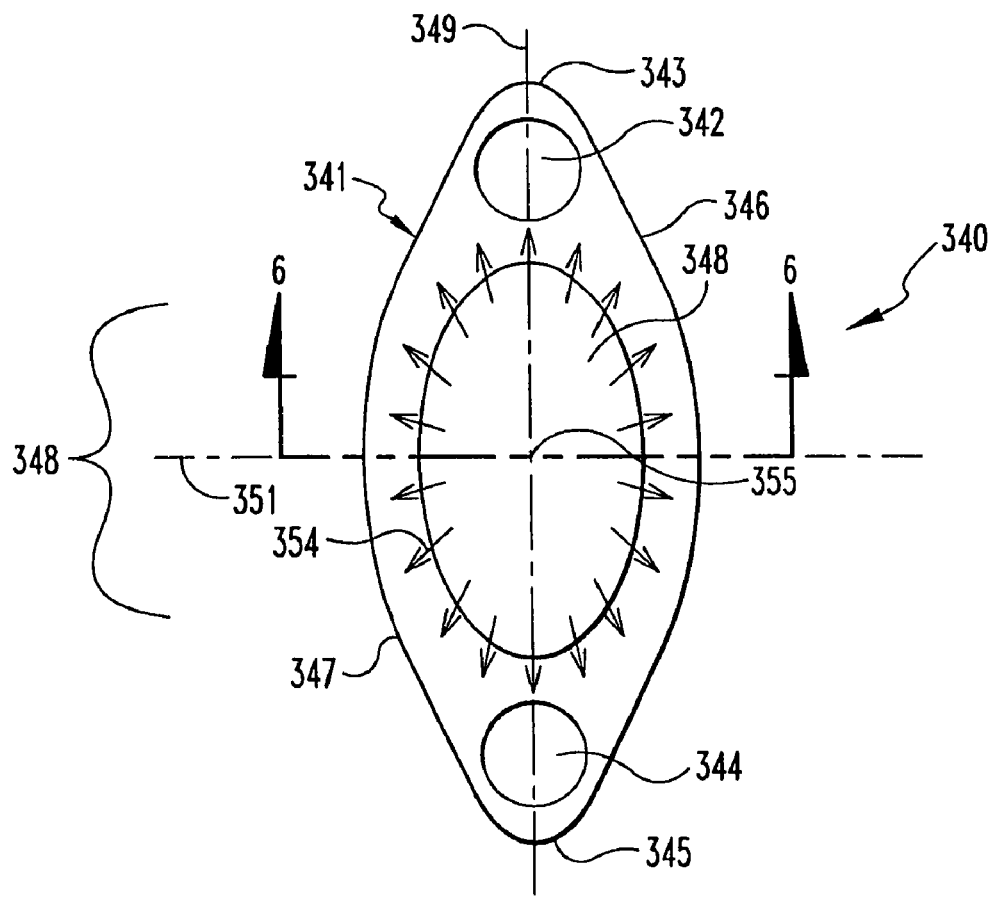
FIG. 5 is a plan view of another embodiment distraction implant.

Referring to FIG. 5, there is provided another embodiment distraction implant 340 including a body 341 with a first hole 342 adjacent a first end 343 and a second hole 344 adjacent a second end 345. Holes 342, 344 can receive first and second anchors, such as anchors 21, 30 discussed above. Body 341 extends along a longitudinal axis 349, and a medial axis 351 divides body 341 into a first portion 346 and a second portion 347. Body 341 includes a variable stiffness mid-portion 348 to provide desired load resistance properties to body 341. In the illustrated embodiment, mid-portion 348 includes a bulbous shape with a maximum thickness at apex 355 at or adjacent the intersection of longitudinal axis 349 and medial axis 351. Mid-portion 348 could also be provided with pyramidal or other enlarged shapes.

Figure 6:
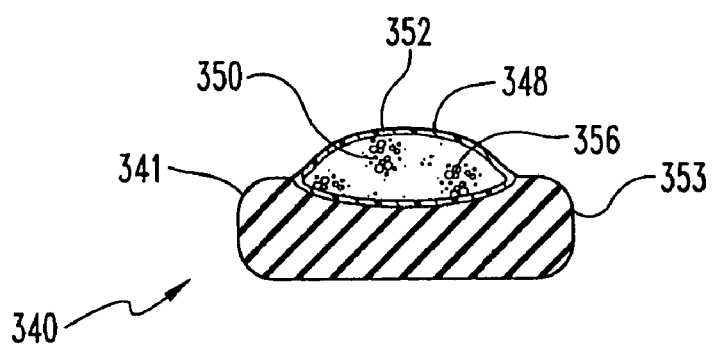
FIG. 6 is a sectional view through line 6-6 of FIG. 5.

As shown in FIG. 6, mid-portion 348 includes an upper member 352 extending from and formed at each end with base portion 353 of body 341. Upper member 352 can form a chamber 350 with a base portion 353 into which a secondary device 356 can be positioned. Secondary device 356 can imbibe fluid or water over time to apply and/or maintain a distraction force to the adjacent bony portions. Arrows 354 (FIG. 5) are representative of the outwardly directed pressure applied in chamber 350 by the fluid as compressive forces are applied to body 341. The osmotic gradient into secondary device 356 extends in the direction opposite arrows 354, causing secondary device 356 to stiffen and maintain the distraction force over time, or to expand over time to increase the distraction force applied by distraction implant 340. Secondary device 356 can be provided in the form of a sponge, foam, or other suitable osmotic material. Other embodiments contemplate a fluid, gel, foam liquid or other flowable material in chamber 350 without a secondary device 356.

Referring to FIG. 7, there is shown adjacent bony portions for one specific application of the distraction implant which includes a spinal column segment 500. Spinal column segment 500 includes a first vertebra 502, a second vertebra 504 and a third vertebra 506. A first disc space 508 is located between first vertebra 502 and second vertebra 504, and a second disc space 510 is located between second vertebra 504 and third vertebra 506. A first anchor 21 is engaged with first vertebra 502, a second anchor 30 is engaged with second vertebra 504, and a third anchor 430 is engaged with third vertebra 506. As discussed above with respect to anchors 21 and 30, third anchor 430 can include a distal bone engagement portion 432 engageable to vertebra 506, and a proximal attachment portion 434 extending therefrom for attachment of a distraction implant.

In FIG. 7 spinal column segment 500 is viewed in the anterior-posterior direction, and is deformed with a lateral concave curvature along one side thereof, indicative of scoliosis. As shown in FIGS. 8 and 9, a distraction implant system 420 is attachable to anchors 21, 30, and 430 in order to correct the concave curvature of the spinal column segment 500. Distraction implant system 420 includes first distraction implant 40 and a second distraction implant 440, which can be identical to first distraction implant 40. First implant 40 is attached intravertebrally to first anchor 21 and the second anchor 30. Second implant 440 is attached intravertebrally to second anchor 30 and third anchor 430.

Attaching implants 40, 440 laterally along the anterior portion of the vertebral bodies avoids the nerves and muscle tissue associated with the posterior vertebral elements, and the vasculature and delicate ligaments along the anterior face of the vertebrae. In addition, the distractive force of the implant is applied directly along the concavely curved side of the vertebral bodies to push the vertebrae into alignment.

As distraction implant 40 is attached to anchors 21 and 30, it can be placed in its second condition by, for example, compressing it and attaching it to proximal attachment portions 24, 34 of anchors 21, 30. Similarly, implant 440 can be compressed and attached to proximal attachment portions 34, 434 of anchors 30, 430. The attached distraction implants 40, 440 tend to reform from their second condition to their first condition, resulting in distraction forces being applied between respective ones of the anchors attached to the implant, correcting the concave curvature of spinal column 500 toward a normal condition as shown in FIG. 9.

In FIG. 7, arrows 512 and 514 indicate distraction forces being applied between anchors 21 and 30, and arrows 516, 518 indicate distraction forces being applied between anchors 30 and 430. Such distraction forces can be applied between the anchors before attaching implants 40, 440 to correct the concave curvature to the spinal column 500. Distraction implants 40, 440 can be attached to maintain and/or increase distraction between the adjacent vertebral bodies through the corresponding anchors, correcting the concave curvature of spinal column 500 toward a normal condition as shown in FIG. 9.

Figure 12:
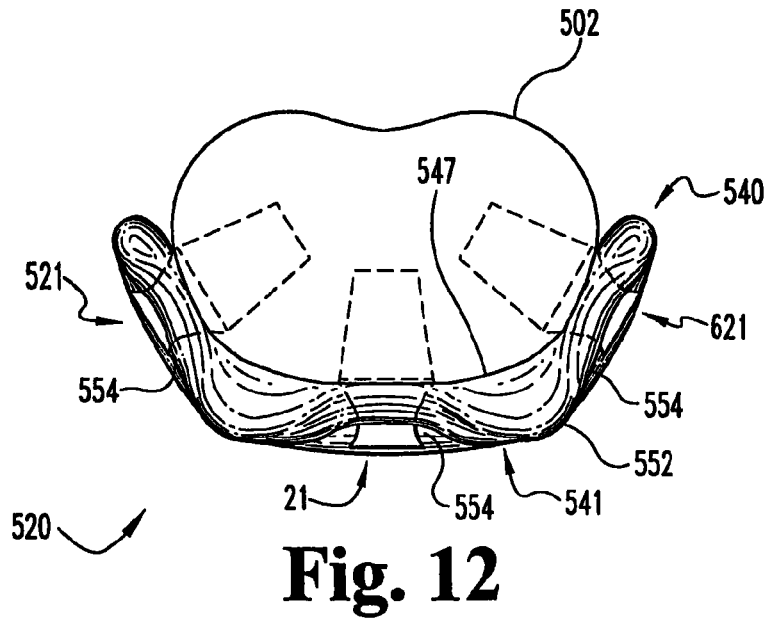
FIG. 12 is a plan view of the spinal column segment and distraction implant of FIG. 11.
Figures 10, 11:
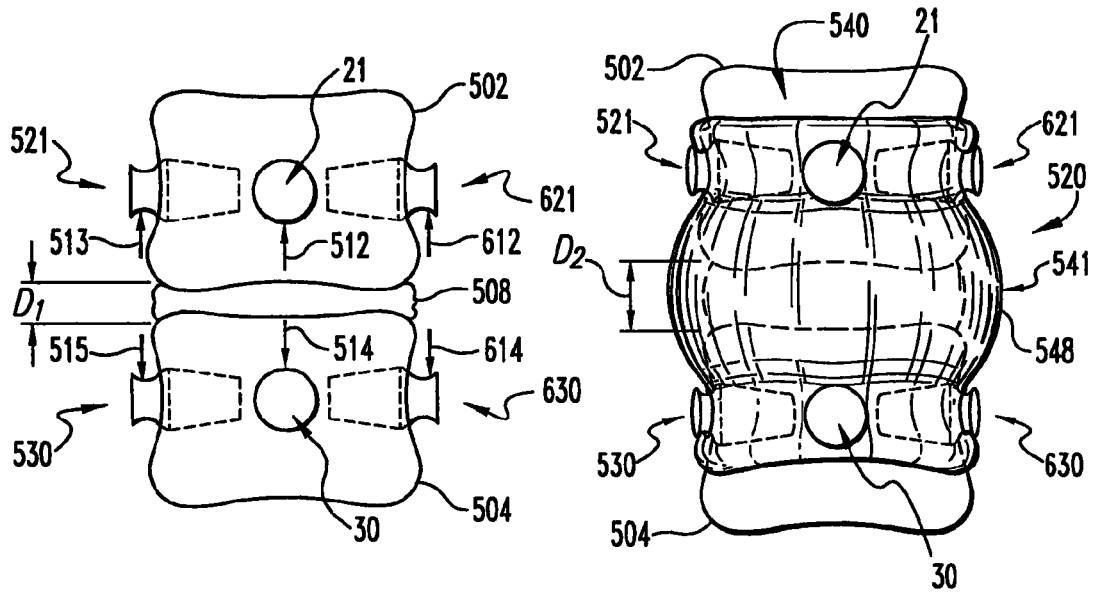
FIG. 10 is an elevation view of a spinal column segment in the anterior-posterior direction having anchors secured thereto.
FIG. 11 is the elevation view of the spinal column segment of FIG. 10 with another embodiment distraction implant secured thereto.

Referring now to FIGS. 10-12, another embodiment distraction implant system 520 is provided. In FIG. 10, spinal column segment 500 includes first vertebra 502 and second vertebra 504 with the disc space 508 therebetween. Disc space 508 is collapsed such that the normal or desired spacing between vertebrae 502, 504 is not provided, as indicated in FIG. 10 by D1. A first anchor 21 is engaged along the anterior portion of vertebra 502, and second and third anchors 521, 621 are engaged laterally or obliquely on opposite sides of vertebra 502. Similarly, vertebra 504 includes a fourth anchor 30 engaged anteriorly thereto, and fifth and sixth anchors 530, 630 are engaged laterally or obliquely on opposite sides of vertebra 504.

In order to provide a distracted disc space 508 with a distracted disc space height indicated by D2 in FIG. 11, distraction forces 512, 513 and 612 can be applied to anchors 21, 521 and 621, respectively, engaged to vertebra 502. Distraction forces 514, 515 and 614 can be applied to anchors 30, 530, and 630, respectively, engaged to vertebra 504. Such distraction forces can be applied by attachment of one or more distraction implants, and/or with a distraction instrument prior to attachment of the one or more distraction implants. By distributing the anchors about the vertebral bodies 502, 504, disc space 508 can be distracted to a uniform height across its width.

A distraction implant 540 is shown in FIG. 11 that is attachable to anchors 21, 521, 621 and anchors 30, 530, 630. In the illustrated embodiment, distraction implant 540 is provided with a U or horseshoe shape at least along its lower surface 547 extending at least partially around each of the vertebrae 502, 504 and also between vertebrae 502, 504 as shown in FIG. 12. The opposite upper surface 552 can be provided with recesses 554 around each of the anchor holes to allow system 520 to maintain a low profile extending from the vertebrae 502, 504. Distraction implant 540 can be provided with a body 541 having properties that allow its to be placed in a second condition and return toward a first condition after attachment to exert a distraction load between respective ones of the anchors engaged to vertebrae 502, 504 and restore and maintain the desired disc space height D2 while allowing motion between vertebrae 502, 504. In one embodiment, body 541 includes an enlarged mid-portion with a bulbous or rounded shape, and is comprised of a flexible material that is compressible to provide implant 540 in a second condition and sufficiently elastic to return toward its first, uncompressed condition to exert a distraction force.

Referring to FIGS. 13-14, there is shown another embodiment distraction implant 700. Distraction implant 700 includes a body 702 extending from a first end 704 to an opposite second end 706. First end 704 includes a hole 710 and second end 706 includes a hole 712 to facilitate intravertebral attachment to a vertebral body with, for example, a first anchor 21 and a second anchor 30 as discussed above with respect to system 20. Ends 704, 706 can each be enlarged relative to body 702 to form the respective holes 710, 712 to receive an anchor therethrough. It is also contemplated that either of body 702 or holes 710, 712 and the corresponding anchors can be sized so that ends 704, 706 are not enlarged relative to body 702.

First hole 710 is spaced a distance 714 from second hole 712 along longitudinal axis 701, and a gap is formed therebetween along longitudinal axis 701 to facilitate movement of first and second ends 704, 706 toward and away from one another in response to compression, expansion, deformation or transformation of body 702. Distance 714 can be of sufficient length to extend across at least one spinal disc space so the ends 704, 706 can be attached to respective ones of adjacent vertebral bodies. It is also contemplated that length 714 can be provided such that body 702 extends across one or more vertebrae, and ends 704, 706 can be attached to provide multi-level distraction. Implant 700 further includes an overall width 718 between longitudinal axis 701 and an outer wall surface 705 of body 702.

It is contemplated that implant 700 can be positioned along a concavely curved portion of the spine, such as the lateral or antero-lateral portion of a scoliotic spine, and is adapted to exert a distraction force between adjacent anchors to treat the concave curvature. Body 702 is curved along a semi-circular path between ends 704, 706, and includes a concave first surface 703 and an opposite convex second, outer surface 705. Body 702 includes a first width 708 between first and second surfaces 703, 705. Body 702 further includes opposite third and fourth surfaces 707, 709 extending between first surface 703 and second surface 705. Third and fourth surface 707, 709 include a second width 711 extending therebetween. When secured to the spinal column, it is contemplated that one of the third and fourth surfaces 707, 709 will be positioned adjacent the spinal column, and the other of third and fourth surface 707, 709 will face away from the spinal column.

In one application for distraction implant 700, and the other distraction implant embodiments discussed herein, implant 700 includes a first condition and is formed to a second condition by moving ends 704, 706 toward one another. In the second condition, ends 704, 706 are attached to anchors engaged to vertebrae or other structures along the concavely curved portion of the spine. Distraction implant 700 then reforms toward its first condition to exert a distraction force between the anchors engaged thereto to correct and/or maintain the concavely curved portion of the spine in the desired alignment. The gap between ends 704, 706 formed by laterally offsetting body 702 relative to longitudinal axis 701 facilitates movement of ends 704, 706 toward one another to obtain the second condition. In addition, the gap between ends 704, 706 facilitates flexing of body 702 in the first condition to permit a limited range of motion for the vertebral level(s) to which implant 700 is engaged.

Distraction implant 700 can be at least partially formed of a shape-memory material that exhibits pseudoelastic characteristics or behavior at about human body temperature. In one embodiment, the implant 700 is formed of the shape-memory material. However, it should be understood that only a portion between ends 704, 706 may be at least partially formed of the shape-memory material, with the ends 704, 706 formed of any suitable biocompatible material, such as, for example, stainless steel or titanium.

SMAs exhibit a "shape-memory" characteristic or behavior in which a particular component formed of a shape-memory alloy ("SMA") is capable of being deformed from an initial "memorized" shape or configuration to a different shape or configuration, and then reformed back toward its initial shape or configuration. The ability to possess shape-memory is a result of the fact that the SMA undergoes a reversible transformation from an austenitic state to a martensitic state. If this transformation occurs due to a change in temperature, the shape-memory phenomena is commonly referred to as thermoelastic martensitic transformation. If the martensitic transformation occurs due to the imposition of stress, the shape-memory phenomena is commonly referred to as stress-induced martensitic transformation. Both types of transformations are contemplated herein.

SMAs are known to display a superelastic phenomena or rubber-like behavior in which a strain attained beyond the elastic limit of the SMA material during loading is recovered during unloading. This superelastic phenomena occurs when stress is applied to an SMA article at a temperature slightly higher than the temperature at which the SMA begins to transform into austenite (sometimes referred to as the transformation temperature). When stressed, the article first deforms elastically up to the yield point of the SMA material (sometimes referred to as the critical stress). However, upon the further imposition of stress, the SMA material begins to transform into stress-induced martensite or "SIM". This transformation takes place at essentially constant stress, up to the point where the SMA material is completely transformed into martensite. When the stress is removed, the SMA material will reform back into austenite and the article will return to its original, pre-programmed or memorized shape. This phenomena is sometimes referred to as superelasticity or pseudoelasticity. It should be understood that this phenomena can occur without a corresponding change in temperature of the SMA material.

Shape-memory materials can also be pliable and can typically be readily reshaped at temperatures below their transformation temperature range. Such articles can be trained to have a pre-programmed shape (commonly referred to as a "memorized shape") which the article will form into when the shape-memory material reaches a temperature above its transformation temperature range. After reaching such a temperature, the article will attempt to form to its pre-programmed, memorized shape. In so doing, the article converts heat energy into mechanical work.

There is a wide variety of shape-memory materials suitable for use with the distraction implants, including shape-memory metal alloys (e.g., alloys of known metals, such as, for example, copper and zinc, nickel and titanium, and silver and cadmium) and shape-memory polymers. While there are many alloys which exhibit shape-memory characteristics, one of the more common SMAs is an alloy of nickel and titanium. One such alloy is nitinol, a bio-compatible SMA formed of nickel and titanium. Nitinol is well suited for the particular application of the distraction implants because it can be programmed to undergo a stress-induced martensitic transformation or thermoelastic martensitic transformation at about normal human body temperature (i.e., at about 35-40 degrees Celsius). Moreover, nitinol has a very low corrosion rate and excellent wear resistance, thereby providing an advantage when used as a support structure within the human body. Additionally, implant studies in animals have shown minimal elevations of nickel in the tissues in contact with the nitinol material. It should be understood, however, that other SMA materials that exhibit superelastic characteristics are contemplated as being within the scope of the invention.

Techniques are contemplated that are suited for distraction implant 700 made from shape memory material. It should be understood that such techniques are also applicable to the other distraction implant embodiments discussed herein. The distraction implant ends, such as ends 704, 706 of implant 700, are moved toward one another to bend body 702 and place shape memory material comprising at least a portion of body 702 in a SIM condition. Body 702 is maintained in this SIM condition, and the ends 704, 706 of implant 700 are attached to vertebrae or other structures along the concavely curved portion of the spine with anchors. The stress on body 702 is then removed, and the engaged distraction implant 700 reforms back into an austenitic state toward its original shape, exerting a distraction force between the anchors engaged thereto to correct and/or maintain the concavely curved portion of the spine in the desired alignment. The gap between ends 704, 706 formed by laterally offsetting body 702 relative to longitudinal axis 701 facilitates movement of ends 704, 706 toward one another to obtain the SIM state or condition, and facilitates flexing of body 702 in the austenetic state to permit a limited range of motion for the vertebral level(s) to which implant 700 is engaged.

In order to achieve additional distraction force and increased stiffness to reduce spinal motion, multiple distraction implants 700 can be stacked one upon the other, and engaged to the concavely curved portion of the spinal column with the same bone anchor at each end. The bodies 702 of the stacked implants 700 can be arranged to be laterally offset to the same side of longitudinal axis 701, or arranged to be laterally offset to opposite sides of longitudinal axis 701. Multiple distraction implants 700 can also be spaced longitudinally and engaged along the spinal column in order to provide distraction at multiple levels. Different levels of the spinal column can be distracted with one implant 700 or differing numbers of stacked implants 700 to provide differing distraction forces and stiffness properties for the implant system along the spinal column.

One or both of the ends 704, 706 of implant 700 can be rigidly secured to the adjacent bone anchor, or allowed to rotate relative thereto. By allowing the ends 704, 706 to rotate, the distraction force will be directed primarily in the direction of movement of ends 704, 706 away from one another as body 702 reforms to the first condition. If one or both of the ends 704, 706 is fixed to the bone anchor, compound forces on the anchor are generated. The compound forces will include a component extending transversely to the central axis of the spinal column, and can be employed to align or maintain alignment of adjacent vertebrae in a direction transverse to the central axis of the spinal column in the anterior-posterior direction, such as would be desirable to correct spondylolisthesis.

Other shapes for distraction implant 700 are also contemplated. For example, FIGS. 15 and 16 show a distraction implant 720 similar to distraction implant 700. Distraction implant 720 includes a body 722 extending between a first end 724 and an opposite second end 726. Body 722 includes a semi-oval shape between first and second ends 724, 726. The semi-oval shape for body 722 provides, for implants of identical lengths 714, 734, a reduced overall width 738 for distraction implant 720 as compared to semi-circular distraction implant 700 having the same overall length.

Figure 17:
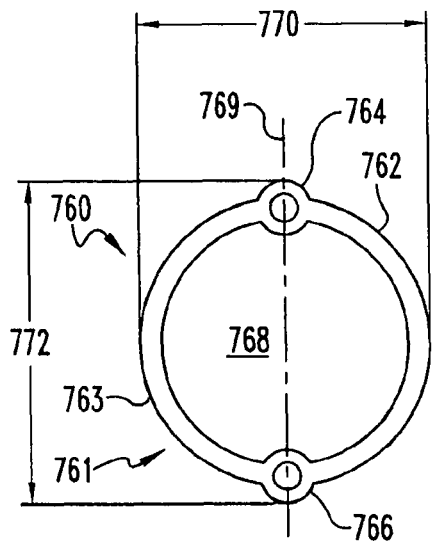
FIG. 17 is an elevation view of another embodiment distraction implant.
Figure 18:
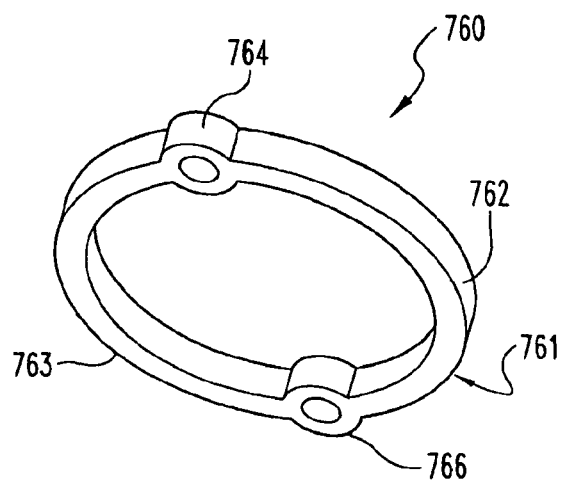
FIG. 18 is a perspective view of the distraction implant of FIG. 17.

Still other embodiments contemplate that the distraction implant include a second body portion extending between the opposite ends to provide additional support to maintain a distraction force. For example, in FIGS. 17 and 18, there is shown distraction implant 760 including a body 761 with a first body portion 762 and a second body portion 763. Body portions 762, 763 each extend between opposite ends 764, 766, where holes can be provided along longitudinal axis 769 to facilitate attachment to vertebrae.

Body 761 forms a circular shape with an opening 768 therethrough, allowing ends 764, 766 to flex or be moved toward one another or away from one another in response to a deformation or change in shape in body portions 762, 763. Body portions 762, 763 are integrally formed with one another at each of the first and second ends 764, 766 to provide a continuous body structure about opening 768.

Figure 19:
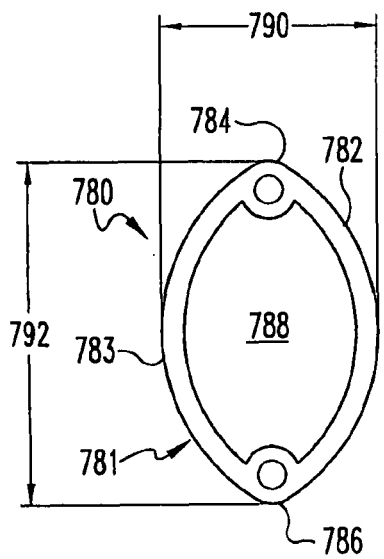
FIG. 19 is an elevation view of another embodiment distraction implant.
Figure 20:
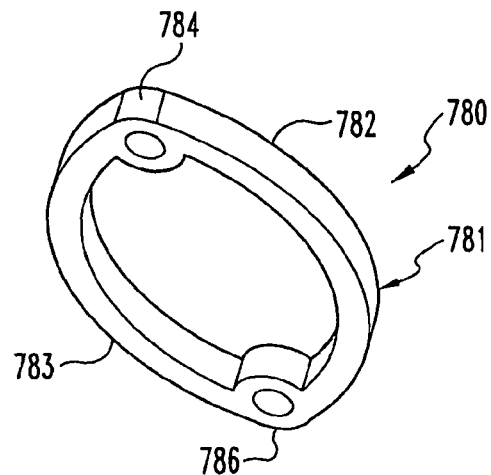
FIG. 20 is a perspective view of the distraction implant of FIG. 19.

In another example, FIGS. 19 and 20 show a distraction implant 780 including a body 781 with a first body portion 782 and a second body portion 783. Body portions 782, 783 each extend between opposite ends 784, 786, where holes can be provided to facilitate attachment to vertebrae. Body 781 forms an oval shape with an opening 788 therethrough, allowing ends 784, 786 to flex or be moved toward one another or away from one another in response to a deformation or change in shape in body portions 782, 783. Body portions 782, 783 are integrally formed with one another at each of the first and second ends 784, 786 to provide a continuous body structure about opening 768.

The oval shape of body 781 of distraction implant 780 includes an overall width 790 between the outer surfaces of body portions 782, 783. Body 781 includes a length 792 between ends 784, 786. Similarly, distraction implant 760 includes a width 770 for its circular shaped body and a length 772 along axis 769 that is substantially the same as width 770. For distraction implant 780, width 790 is less than width 770 of distraction implant 760 for implants having the same lengths 772, 792. Accordingly, distraction implant 780 can be employed if a greater length to width ratio is desired.

Figure 21:
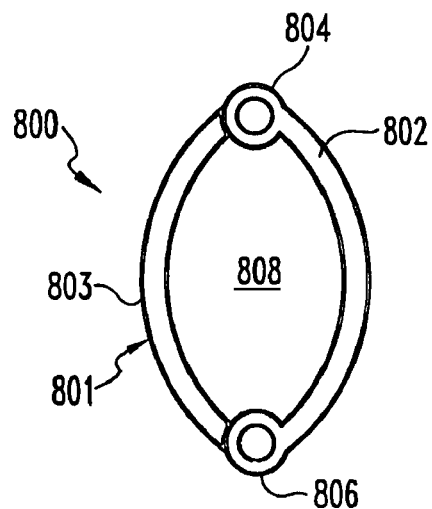
FIG. 21 is an elevation view of another embodiment distraction implant.
Figure 22:
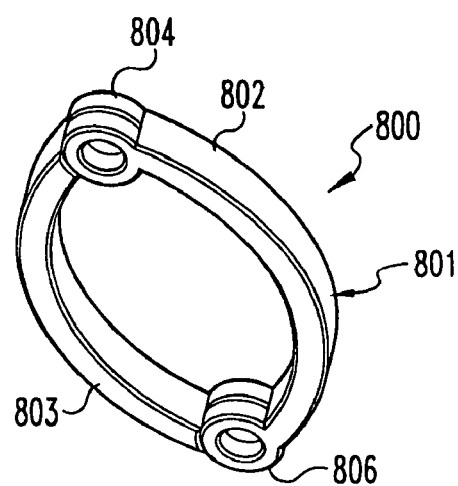
FIG. 22 is a perspective view of the distraction implant of FIG. 21.

FIGS. 21 and 22 show a distraction implant 800 similar to distraction implant 780. Distraction implant 800 includes a body 801 with a first body portion 802 and a second body portion 803. Body portions 802, 803 each extend between opposite ends 804, 806, where holes can be provided to facilitate attachment to vertebrae. Body 801 forms an oval shape with an opening 808 therethrough, allowing ends 804, 806 to flex or be moved toward one another or away from one another in response to a deformation or change in shape in body portions 802, 803. In contrast to distraction implant 780, distraction implant 800 includes a hinged connection at one or both of the ends 804, 806 to allow body portions 802, 803 to move independently relative to one another. The hinged connections facilitates movement of ends 804, 806 toward and away from one another since body portions 802, 803 are not required to bend or deform adjacent ends 804, 806.

Figure 23:
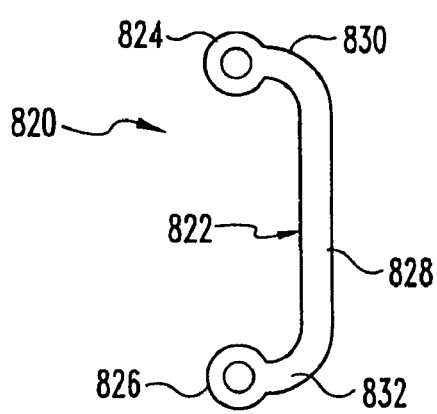
FIG. 23 is an elevation view of another embodiment distraction implant.
Figure 24:
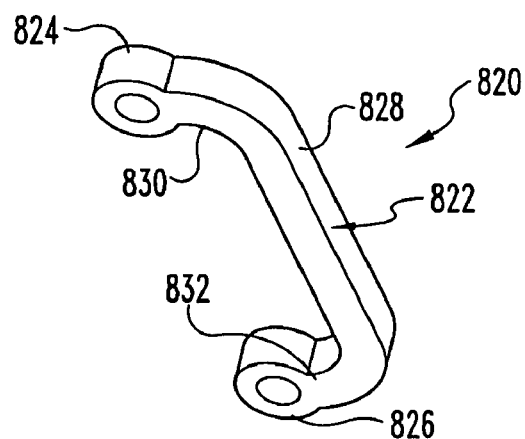
FIG. 24 is a perspective view of the distraction implant of FIG. 23.

Other shapes for the distraction implants 760, 780, 800 are also contemplated, including circular, rectangular, square, diamond, corrugated, polygonal, or other suitable shape. In addition, distraction implants 700, 720 can also be provided with other shapes. For example, FIGS. 23-24 show a distraction implant 820 including a body 822 extending between a first end 824 and an opposite second end 826. Body 822 is offset laterally from ends 824, 826 to facilitate movement of ends 824, 826 toward and away from one another in response to compression, deformation or transformation of body 822. Body 822 includes a linear portion 828 and a pair of angled portions 830, 832 at opposite ends of linear portion 828. Angled portions 830, 832 extend from linear portion 828 to respective ones of the ends 824, 826 to offset linear portion 828 therefrom. Other embodiments contemplated that body 822 can include multiple linear segments interconnected by angled portions, multiple angled portions interconnected with one another, and combinations of linear, angled and arcuate or curved portions between ends 824, 826.

Figure 25:
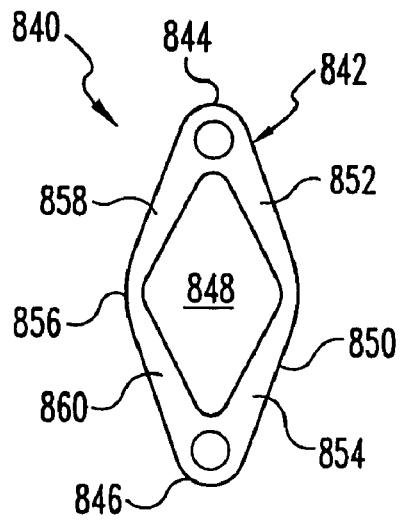
FIG. 25 is an elevation view of another embodiment distraction implant.
Figure 26:
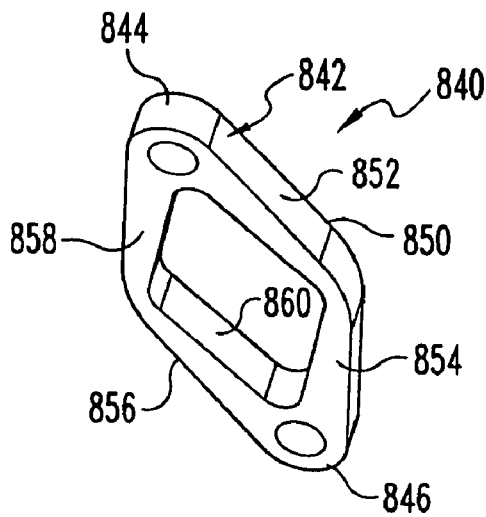
FIG. 26 is a perspective view of the distraction implant of FIG. 25.

In FIGS. 25-26 there is shown distraction implant 840 including a body 842 extending between opposite ends 844, 846. Body 842 includes a first body portion 850 and a second body portion 856 extending along opposite sides of opening 848 and offset laterally from the longitudinal axis of implant 840. Body portion 850 includes a first angled portion 852 extending from first end 844 to a second angled portion 854, which extends from first angled portion 852 to second end 846. Similarly, second body portion 856 includes a first angled portion 858 extending from first end 844 to a second angled portion 860, which extends from first angled portion 858 to second end 846. The junction of angled portions 852, 854 and angled portions 858, 860 are offset laterally from ends 844, 846, providing body 842 with a diamond shape about opening 848. The angled portions facilitate movement of ends 804, 806 toward and away from one another in response to compression, deformation or transformation of first and second body portions 850, 856.

Figure 27:
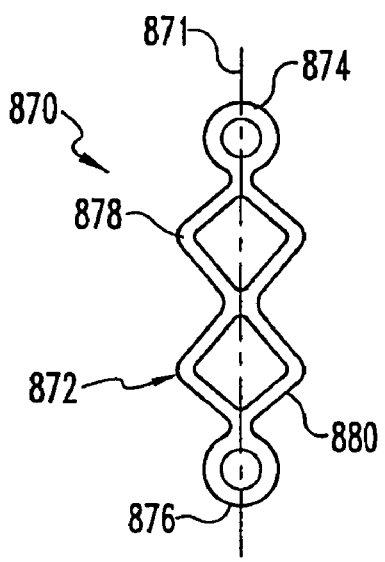
FIG. 27 is an elevation view of another embodiment distraction implant.
Figure 28:
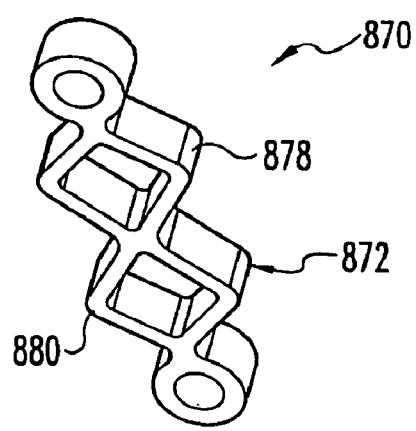
FIG. 28 is a perspective view of the distraction implant of FIG. 27.

Referring to FIGS. 27-28, there is shown distraction implant 870 including a body 872 extending between opposite ends 874, 876. Body 872 includes a multiple body portions 878, 880 linked with one another along the length of body 872 and between ends 874, 876 to form a chain shape. In the illustrated embodiment, body portions 878, 880 are diamond shaped so that the at least a portion of each body portion is offset laterally from longitudinal axis 871. The offsets facilitate movement of ends 874, 876 toward and away from one another in response to compression, deformation, or transformation of all or a portion of the body portion 878, 880. Body portions 878, 880 can also be provided with other shapes, such as circular, oval, square, rectangular or other shapes discussed herein. Furthermore, body portions 878, 880 need not be symmetrical along longitudinal axis 871 of distraction. For example, body portions 878, 880 can be open along or adjacent longitudinal axis 871 to form a zigzag or corrugated shape along longitudinal axis 871.

It is contemplated the implants described herein can be used for the correction of spinal deformities, such as by distracting a concavely curved portion of the spinal column. The distraction implants can be positioned along surfaces of the spinal column segment comprising the concavely curved portion of the spinal column segment to directly counteract the concave curvature with distraction forces. The distraction implants can be employed in fusionless treatment of scoliosis either alone or as an adjunct to a convexly applied fusionless scoliosis treatment system. It is further contemplated the implants described herein can be used for intravertebral distraction of adjacent vertebrae across a disc space in which the disc space is collapsed, or the relationship or spacing between the vertebra is desired to be altered or maintained. The distraction implants can stabilize the spinal column segment while allowing segmental motion. It is further contemplated that one or more distraction implants can be attached to any bony portion in which distraction and motion between adjacent bony portions is desired.

While the invention has been illustrated and described in detail in the drawings and foregoing description, the same is to be considered as illustrative and not restrictive in character, and that all changes and modifications that come within the spirit of the invention are desired to be protected.

What is claimed is:

1. An implant system for distracting first and second vertebrae of a spinal column segment, comprising:
    a first anchor engageable to the first vertebra;
    a second anchor engageable to the second vertebra; and
    a body including first and second ends attached to respective ones of said first and second anchors, wherein said body extends along a longitudinal axis from said first end to said second end, said body including a first portion extending between said first and second ends, wherein said first and second anchors are located on said longitudinal axis and extend from said first and second ends in a first direction from said longitudinal axis of said body and said first direction and said longitudinal axis define a plane extending into the first and second vertebrae with said first portion being offset laterally from said longitudinal axis and said plane to form a gap between said first and second ends, wherein said body is further comprised of a shape memory alloy between said first and second ends, said shape memory alloy having an initial configuration and an implantation configuration and said body is attached to said first and second anchors in said implantation configuration and said shape memory alloy is structured to reform toward said initial configuration to normally bias said first and second anchors away from one another while permitting motion of the spinal column segment when said first and second anchors are engaged to the first and second vertebrae.

2. The implant of claim 1, wherein said first portion of said body includes one of a semi-circular and semi-oval shape that extends between said first and second anchors.

3. The implant of claim 1, wherein said first portion of said body includes a semi-rectangular shape that extends between said first and second anchors.

4. The implant of claim 1, wherein said first portion of said body includes a triangular shape that extends between said first and second anchors.

5. The implant of claim 1, wherein said body includes a second portion extending between said first and second ends offset laterally from said longitudinal axis in a direction opposite said first portion of said body, said first and second portions forming an opening through said body between said first and second ends.

6. The implant of claim 5, wherein said first and second portions of said body form a shape between said first and second ends that is one of a circular shape, an oval shape, a diamond shape, and a chain-shape.

7. The implant of claim 5, wherein said first and second portions of said body are hingedly coupled together adjacent at least one of said first and second ends so that said first and second portions move independently of one another in response to loading from the spinal column segment.

8. The implant of claim 1, further comprising a second body separate from and stacked on said body, said second body including first and second ends attached to respective ones of said first and second anchors, wherein said second body extends along a longitudinal axis from said first end to said second end of said second body, said second body including a first portion extending between said first and second ends that is offset laterally from said longitudinal axis to form a gap between said first and second ends, wherein said second body is further comprised of a shape memory alloy between said first and second ends, said shape memory alloy having an initial configuration and an implantation configuration and said second body is attached to said first and second anchors in said implantation configuration and said shape memory alloy is structured to reform toward said initial configuration to normally bias said first and second anchors away from one another while permitting motion of the spinal column segment when said first and second anchors are engaged to the first and second vertebrae.

9. The implant of claim 1, wherein said first and second ends each include a hole extending therethrough in a transverse orientation to said longitudinal axis and said first and second anchors extend through a respective one of said holes.

10. The implant of claim 9, wherein said first and second ends each include a portion that is enlarged relative to said body and said holes extend through said enlarged portion.

11. The implant of claim 1, wherein said body includes a linear portion extending along said longitudinal axis in a direction between said first and second ends, and said body further includes first and second angled portions extending from said linear portion to respective ones of said first and second ends.

12. An implant system for distracting first and second vertebrae of a spinal column segment, comprising:
    a first anchor engageable to the first vertebra;
    a second anchor engageable to the second vertebra; and
    a body with a length along a longitudinal axis between a first end and an opposite second end, each of said first and second ends being located on said longitudinal axis and are attached to respective ones of said first and second anchors, said body including a first portion extending between said first and second ends, said first portion being offset laterally from said longitudinal axis to form a gap between said first and second ends, wherein said first portion includes a concave surface facing said longitudinal axis and a convex surface opposite of said concave surface, said first portion further including a bottom surface and a top surface opposite said bottom surface, said top and bottom surfaces each extending between said concave and convex surfaces, wherein said bottom surface is planar and faces the first and second vertebrae and said top surface faces away from the first and second vertebrae when said first and second anchors engage said body to the first and second vertebrae, said body further said being comprised of a shape memory material including a first condition and a second condition, said body being attached to said first and second anchors in said second condition and said shape memory material changes phase to reform toward said first condition to normally bias said first and second anchors away from one another while permitting relative motion between said first and second anchors when said first and second anchors are engaged to the first and second vertebrae.

13. The implant of claim 12, wherein said body includes a second portion extending between said first and second ends, said second portion being offset laterally from said longitudinal axis in a direction opposite said first portion, said first and second portions forming an opening through said body between said first and second ends.

14. The implant of claim 13, wherein said first and second portions of said body are each integrally formed with said first and second ends and form a continuous, one-piece body structure around said opening.

15. The implant of claim 13, wherein said first and second portions of said body are hingedly connected to one another at each of said first and second ends so that said first and second portions move independently of one another in response to loading from the spinal column segment.

16. The implant of claim 13, wherein said first and second portions of said body form a plurality of diamond shaped openings between said first and second ends.

17. The method of claim 12, wherein said shape memory material is structured to reform from said second condition toward said first condition by increasing a temperature of said shape memory material.

18. The implant of claim 12, wherein said first and second ends each include a hole extending therethrough in a transverse orientation to said longitudinal axis and said first and second anchors extend through a respective one of said holes.

19. The implant of claim 18, wherein said first and second ends each include a portion that is enlarged relative to said body and said holes extend through said enlarged portion.

20. The implant of claim 12, wherein said body includes a linear portion extending along said longitudinal axis in a direction between said first and second ends, and said body further includes first and second angled portions extending from said linear portion to respective ones of said first and second ends.

* * * * *